United States Patent [19]

Müller et al.

[11] Patent Number: 5,300,505
[45] Date of Patent: Apr. 5, 1994

[54] STABLE SALTS OF 5,10-METHYLENETETRAHYDROFOLIC ACID

[75] Inventors: Hans R. Müller, Schaffhausen; Martin Ulmann, Dachsen; Josef Conti, Schaffhausen, all of Switzerland

[73] Assignee: Eprova Aktiengesellschaft, Schaffhausen, Switzerland

[21] Appl. No.: 957,764

[22] Filed: Oct. 15, 1992

[30] Foreign Application Priority Data

Oct. 15, 1991 [CH] Switzerland .................. 03 019/91-6

[51] Int. Cl.$^5$ ............................................ C07D 475/04
[52] U.S. Cl. ..................................... 514/250; 544/251
[58] Field of Search ............... 544/258, 251; 514/249, 514/250

[56] References Cited

U.S. PATENT DOCUMENTS 3,468,886  9/1969  Mosher et al. ..................... 544/258
5,006,655  4/1991  Müller et al. ..................... 544/258

FOREIGN PATENT DOCUMENTS 0348641  1/1990  European Pat. Off. .
0495204  7/1992  European Pat. Off. .

Primary Examiner—Donald G. Daus
Attorney, Agent, or Firm—Millen, White, Zelano, & Branigan

[57] ABSTRACT

Salts of 5,10-methylene-(6R)-, (6R,S)-, and (6S)-tetrahydrofolic acid with sulfuric acid or a sulfonic acid are stable in solid form and can be used as a constituent and/or as a starting material for the production of pharmaceutical compositions.

10 Claims, No Drawings

STABLE SALTS OF 5,10-METHYLENETETRAHYDROFOLIC ACID

BACKGROUND OF THE INVENTION

This invention relates to novel stable salts of 5,10-methylene-N-[4-[[2-amino-1,4,5,6,7,8-hexahydro-4-oxo-(6R)-, (6R,S)-, or (6S)-pteridinyl)-methyl]amino]-benzoyl]-L-glutamic acid [hereinafter "5,10-methylene-(6R)-, (6R,S)- or (6S)-tetrahydrofolic acid"].

Tetrahydrofolates are the biologically active forms of folic acid (folic acid co-factors).

As pharmaceuticals, tetrahydrofolates are mainly used as the calcium salt of 5-formyl-5,6,7,8-tetrahydrofolic acid (leucovorin), for example, for increasing the therapeutic effect of 5-fluorouracil or, for example, as a rescue substance when using methotrexate in cancer therapy.

In the body, 5-formyl-(6S)-tetrahydrofolic acid is converted to 5,10-methylene-(6R)-tetrahydrofolic acid, which, as a co-factor, forms a cytostatically active, covalent ternary complex: 5-F-dUMP/TS/methylenetetrahydrofolic acid with 5-fluorodeoxyuridine monophosphate (5-F-dUMP) and thymidylate synthetase (TS) formed from 5-fluorouracil (5-FU). See W. A. Bleyer, *Cancer*, Supplement, March 15, 1989, pp. 995-1007, and E. L. R. Stokstad, *Folic Acid Metabolism in Haltha nd Disease* 1990, Wiley-Liss, Inc., p. 9.

It would, therefore, be advantageous to use the cofactor 5,10-methylenetetrahydrofolic acid directly instead of leucovorin (5-formyl-tetrahydrofolic acid). Until now, this undertaking has failed because 5,10-methylenetetrahydrofolic acid and its salts have been unstable and generally of insufficient purity. For example, recrystallization has not been successful because the known salts decompose during recrystallization, resulting in little or no improvement in purity.

Such known salts of 5,10-methylenetetrahydrofolic acid—mainly alkali-, alkaline-earth, and alkanolamine salts—have been described in various publications. For example, B. T. Kaufmann et al., *J. Biol. Chem.* 238, 1498-1500 (1963), described a "relatively pure isomer of 5,10-methylenetetrahydrofolic acid" as alkali salt, confirmed by V. F. Scott et al. in *Biochem. and Biophys. Res. Comm.* 14, 523-526 (1964). An alkanolamine salt (Tris) with a purity of more than 97% was described by J. E. Wright et al., *Cancer Research* 49, 2592-2596 (1989). Also, the precipitation of 5,10-methylenetetrahydrofolic acid by the addition of DCl and the following transformation into the sodium salt was reported in M. Poe et al., *Biochemistry* 18 (24), 5527-5528 (1979). The barium salt of 5,10-methylenetetrahydrofolic acid was disclosed by R. L. Blakey et al. in *The Journal of Biological Chemistry* 238 (9), 3075-3079 (1963). See also EP-A-0 409 125.

SUMMARY OF THE INVENTION

An object of this invention, therefore, is to provide a stable form of 5,10-methylenetetrahydrofolic acid, especially in recrystallizable form.

Another object is to provide a highly pure form of 5,10-methylenetetrahydrofolic acid, and pharmaceutical preparations thereof.

Still another object is to provide processes for providing the desired products.

Upon further study of the specification and appended claims, further objects and advantages of this invention will become apparent to those skilled in the art.

DETAILED DESCRIPTION

It has now surprisingly been found that salts of 5,10-methylene-(6R)-, (6R,S)-, and (6S)-tetrahydrofolic acid can be obtained which have a stability never before achieved, as well as an extraordinarily high purity by reaction of the corresponding diastereomeric form of 5,10-methylenetetrahydrofolic acid, in particular, with sulfuric acid or, alternatively, with sulfonic acids.

The diastereomeric forms of 5,10-methylenetetrahydrofolic acid are preferably prepared from the (6S)-, (6R,S)-, and (6R)-tetrahydrofolic acid sulfate or sulfonic acid salt which has become easily accessible as a result of Swiss Patent Application No. 108 of January 16, 1991, by reaction with formaldehyde In this reaction, natural 5,10-methylene-(6R)-tetrahydrofolic acid is formed from (6S)-tetrahydrofolic acid. That is because the absolute configuration on the C-6 of natural tetrahydrofolic acid is to be specified by S, according J. C. Fontecilla-Camps et al., *J. Amer. Chem. Soc.* 101 (20), 6114-15 (1979), according to the sequence rule, and that on C-6 of natural 5,10-methylenetetrahydrofolic acid is to be specified by R. See R. Kalbermatten et al., *Helv. chim. Acta* 64 (8), 2627 (1981), footnote 4.

The reaction with sulfuric acid or a sulfonic acid is performed in a suitable solvent, preferably water and/or a lower aliphatic, water-soluble carboxylic acid or a lower alcohol, the addition of an alcohol also being used for the precipitation of the sulfate or sulfonate formed.

The products obtained are virtually absolutely stable at room temperature in solid form. They are suitable as constituents of oral pharmaceuticals forms or as a starting material for the production of parenteral pharmaceutical forms. Both the oral and the parenteral pharmaceutical forms are suitable, for example, for cancer therapy, for the treatment of certain forms of anemia, autoimmune diseases, and neural disorders.

The invention accordingly provides salts of (6R)-, (6R,S)-, and (6S)-5,10-methylenetetrahydrofolic acid with sulfuric acid or a sulfonic acid.

Preferred compounds include but are not limited to:

5,10-methylene-(6R)-tetrahydrofolic acid sulfate;
5,10-methylene-(6R,S)-tetrahydrofolic acid sulfate;
5,10-methylene-(6S)-tetrahydrofolic acid sulfate;
5,10-methylene-(6R)-, (6R,S)-, (6S)-tetrahydrofolic acid benzenesulfonate;
5,10-methylene-(6R)-, (6R,S)-, (6S)-tetrahydrofolic acid toluene-4-sulfonate; and
5,10-methylene-(6R)-, (6R,S)-, (6S)-tetrahydrofolic acid methanesulfonate.

The invention further provides a process for the preparation of the salts of 5,10-methylene-(6R)-, (6R,S)-, and (6S)-tetrahydrofolic acid with sulfuric acid or a sulfonic acid which comprises reacting the corresponding diastereomeric form of 5,10-methylenetetrahydrofolic acid with sulfuric acid or a sulfonic acid.

This reaction is preferably performed using 5,10-methylenetetrahydrofolic acid prepared in situ. The reaction is carried out in a solvent which is generally water or a water-miscible organic solvent such as a lower aliphatic carboxylic acid or a lower alcohol.

In addition to sulfuric acid, one may use sulfonic acids as salt-forming agents. Preferred sulfonic acids include, but are not limited to, benzenesulfonic acid, a toluenesulfonic acid, xylenesulfonic acid, nitrobenzenesulfonic acid, chlorobenzenesulfonic acid, nitrotoluenesulfonic acid, naphthalenesulfonic acid, substituted naphthalenesulfonic acid, a camphorsulfonic acid, phenylmethanesulfonic acid, methanesulfonic acid, ethanesulfonic acid, propanesulfonic acid, and butanesulfonic acid.

Ranges of normalities of the sulfuric acid and the sulfonic acids in the process are of minor relevance in the crystallization step. Due to the better solubility of the products in water, any additional water in the crystallization mixture has to be compensated for by the addition of ethanol or similar solvents, wherein the products are less soluble. Preferred ranges of the stoichiometric excess for the sulfuric acid and the sulfonic acids within a wide range, from about molecular equivalent amounts to a few hundred percent excess.

The solvent employed for the isolation of the salts of 5,10-methylenetetrahydrofolic acid is water; a lower aliphatic, water-soluble carboxylic acid such as, for example, acetic acid, lactic acid, formic acid; a water-soluble alcohol such as, for example, methanol, ethanol, isopropanol; or a mixture thereof.

The invention also provides pharmaceutical compositions of the stable salts of 5,10-methylene-(6R)-, (6R,S)-, or (6S)-tetrahydrofolic acid with sulfuric acid or a sulfonic acid, used as a constituent and/or starting material. The conventional techniques used for formulating salts of leucovorin into pharmaceutical forms can be used analogously to make the pharmaceutical compositions of this invention. For increasing the therapeutic effect of 5-fluorouracil, the preferred dosage forms, ranges, and carriers are comparable to forms, ranges, and carriers of leucovorin as 5,10-methylenetetrahydrofolic acid is the active metabolite of leucovorin. Also, for the administration of the pharmaceutical compositions to patients, the same protocol would be used as with salts of leucovorin.

The novel salts of 5,10-methylenetetrahydrofolic acid of this invention can also be used as starting materials for the production of pharmaceutical compositions, for example, by transforming 5,10-methylenetetrahydrofolic acid, e.g., to 5-methylenetetrahydrofolic acid or tetrahydrofolic acid by the addition of a reducing agent within the pharmaceutically formulated product of before starting the formulation process.

Without further elaboration, it is believed that one skilled in the art can, using the preceding description, utilize the present invention to its fullest extent. The following preferred specific embodiments are, therefore, to be construed as merely illustrative and not limitative of the remainder of the disclosure in any way whatsoever.

In the foregoing and in the following examples, all temperatures are set forth uncorrected in degrees Celsius; and, unless otherwise indicated, all parts and percentages are by weight.

The entire disclosure of all applications, patents, and publications, cited herein, and of corresponding Swiss Patent Application No. 03 019/91-6, filed Oct. 15, 1991, are hereby incorporated by reference.

EXAMPLES

Starting Materials

The following starting materials are exemplified in Swiss Patent Application No. 108, filed Jan. 16, 1991, referred to in the examples:

A. (6S)-tetrahydrofolic acid toluene-4-sulfonic acid

According to processes described in the literature, for example, R. L. Blakley et al. (ed.), Folates and Pterins, Volume 1, "Chemistry and Biochemistry of Folates," 1984, pp. 93–104, (6R,S)-tetrahydrofolic acid prepared in situ is directly reacted further with toluene-4-sulfonic acid:

50 g of folic acid are suspended at 25° C. under nitrogen in 200 ml of water, for example, according to C. Temple, J. Med Chem., 22, 731 (1979). The pH of the solution is adjusted to 12 using about 40 g of 30% sodium hydroxide solution. After addition of 25 g of sodium borohydride (630 mol %) in 110 ml of water, the reaction mixture is heated to 70–75° C. and kept at this temperature for 90 minutes. 30 g of toluene-4-sulfonic acid (150 mol%), dissolved in 200 ml of glacial acetic acid, are added dropwise to the solution of (6R,S)-tetrahydrofolic acid sodium salt thus obtained after cooling to 25° C. The pH of the solution is then adjusted to below 1 using 96 g of 37% hydrochloric acid. After 12 hours, the precipitated product is filtered off and washed with acetic acid/water, then with ethanol.

32.9 g of toluene-4-sulfonic acid addition salt of (6S)-tetrahydrofolic acid having a purity of 82% and a (6S)-content of 95.4% are obtained, determined by means of HPLC.

3.0 g of the (6S)-tetrahydrofolic acid-toluene-4-sulfonic said addition salt thus obtained are suspended at 25° C. under nitrogen in 30 ml of water and adjusted to pH 11.6 with about 3 g of 30% sodium hydroxide solution. 0.9 g of toluene-4-sulfonic acid (120 mol%), dissolved in 36 ml of glacial acetic acid, is added dropwise to the solution thus obtained. The pH of the solution is then adjusted to below 1 with 2.2 g of 37% hydrochloric acid. After 12 hours, the precipitated product is filtered off and washed with acetic acid/water, then with ethanol.

1.81 g of toluene-4-sulfonic acid solution salt of (6S)-content of 98.9% are obtained, determined by means of HPLC.

B. (6S)-tetrahydrofolic acid benzene sulfonate

By the replacement of toluene-4-sulfonic acid in the previous example (A) by the equivalent amount of benzenesulfonic acid, the benzenesulfonic acid addition salt of (6S)-tetrahydrofolic acid can be prepared in a similar manner.

32.2 g of benzenesulfonic acid addition salt of (6S)-tetrahydrofolic acid having a purity of 80% and a (6S)-content of 94.2% are obtained.

C. (6S)-tetrahydrofolic acid sulfate 30 ml of 2M sulfuric acid are initially introduced at 60° C. with 130 ml of water containing 0.2% of 2-mercaptoethanol and 164 ml of glacial acetic acid. 20 go of pure (6R,S)-tetrahydrofolic acid are introduced in the course of 5 minutes. The resulting solution is cooled to 50° C. After 1 hour, the precipitated product is filtered off and washed with water/glacial acetic acid, then with ethanol.

11.0 g of sulfuric acid addition salt of (6S)-tetrahydrofolic acid having a (6S)-content of 65.5% are obtained, determined by means of HPLC.

By recrystallizing 10 g of sulfuric acid addition salt of (6S)-tetrahydrofolic acid twice from dimethylformamide/water 1:3, 3.9 g of sulfuric acid addition salt of (6S)-tetrahydrofolic acid having a (6S)-content of 94.3% are obtained, determined by means of HPLC.

Example 1: 5,10-methylene-(6R)-THF sulfate

A. Preparation of 5,10-methylene-(6R)-tetrahydrofolic acid 100 g of pure (6S)-tetrahydrofolic acid benzenesulfonate prepared, for example, by the method described in Swiss Patent Application No. 108, filed January 16, 1991, are suspended in water. The pH is brought to 7.5 by addition of I N sodium hydroxide solution. 15 ml of 37% strength aqueous formaldehyde solution are then added, and the mixture is adjusted to pH 2.5 with 2 N sulfuric acid. The 5,10-methylene-(6R)-tetrahydrofolic acid formed precipitates and is filtered off.

Amount: 74 g.

B. Preparation of 5,10-methylene-(6R)-tetrahydrofolic acid sulfate 74 g of 5,10-methylene-(6R)-tetrahydrofolic acid are dissolved in 370 ml of glacial acetic acid and introduced dropwise into a solution of 97 ml of 4 N aqueous sulfuric acid in 200 ml of glacial acetic acid. Thereafter, 5,10-methylene-(6R)-tetrahydrofolic acid sulfate of the formula methylene-(6R)-THF.$H_2SO_4$ crystallizes out. After addition of 500 ml of ethanol, the product is filtered off. The product is precipitated from formic acid with ethanol having a ratio of 1:1 to 1:4 or from acetic acid with ethanol/$H_2SO_4$ having a ratio of 1:1:1 to 1:4:1.

Yield: 71 g; purity 98% (determined by HPLC). $[\alpha]^{25}_D = +120°$ (c=1% in DMF).

Solubilities: methylene-(6R)-THF.$H_2SO_4$ is fairly poorly soluble in water, soluble in boiling 50% acetic acid, and easily soluble in hot glacial acetic acid.

Example 2: 5,10-methylene-(6R)-THF sulfate 20 g of (6S)-tetrahydrofolic acid sulfate prepared according to Swiss Patent Application No. 108, filed Jan. 16, 1991, are suspended in water. The pH is adjusted to 8.6 by addition of 2 N sodium hydroxide solution. 3.6 ml of 37% strength aqueous formaldehyde solution are then added. After 15 minutes, the solution obtained is stirred into a solution of ml of 2 N sulfuric acid in 100 ml of glacial acetic acid. The precipitated product is filtered off and washed with ethanol.

14 g of the title compound are obtained in this way.

Purity, determined by means of HPLC: 98.7% methylene-(6R)-THF.$H_2SO_4$.

Example 3: 5,10-methylene-(6s)-THF sulfate 5 g of (6R)-tetrahydrofolic acid are dissolved in 36 ml of 1 N sodium hydroxide solution, and the solution is treated with 1.5 ml of 36% strength formaldehyde at pH 8. After 10 minutes, the reaction solution obtained is stirred in 20 ml of 2 N sulfuric acid in 25 ml of glacial acetic acid. After addition of 30 ml of ethanol, the precipitated product is filtered off.

3.8 g of the title compound are obtained.

Purity: 96% methylene-(6S)-TH sulfate.

Example 4: 5,10-methylene-(6R)-THF sulfate 100 g of (6S)-tetrahydrofolic acid are dissolved in warm glacial acetic acid. The solution is treated with 20 ml of 37% strength formaldehyde, subjected to clarifying filtration and salified with 180 ml of 4 N aqueous sulfuric acid. After addition of 1.5 l of ethanol, the precipitated product is filtered off. It consists of the title compound.

Purity: 97% methylene-(6R)-THF.$H_2SO_4$.

Example 5: 5,10-methylene-(6R)-THF Sulfate

50 G of (6S)-tetrahydrofolic acid sulfate prepared, for example, according to Swiss Patent Application No. 108, filed Jan. 16, 1991, having a purity of 99.8% (6S)-THF.$H_2SO_4$ suspended in water, are dissolved by addition of 200 ml of 2 N sodium hydroxide solution, and the solution lo is treated with 7.5 ml of 37% strength formaldehyde. The reaction solution is introduced dropwise into a mixture of 275 ml of 2 N sulfuric acid and 275 ml of glacial acetic acid. Methylene-(6R)-THF.$H_2SO_4$ crystallizes out and is filtered off and washed with ethanol.

Yield: 45 g of colorless product.

HPLC analysis: 99.6% methylene-(6R)-THF.$H_2SO_4$.

Example 6: 5,10-methylene-(6R)=THF benzenesulfonate

Analogously to above, 27.1 g of (6S)-tetrahydrofolic acid benzenesulfonate are dissolved in water by addition of 25.8 ml of 5 N sodium hydroxide solution. 3.5 ml of 37% strength aqueous formaldehyde are then added, and the mixture is stirred for 10 minutes.

The reaction solution obtained is introduced dropwise into a solution of 21.07 g of benzenesulfonic acid in 100 ml of water. The precipitated product is filtered off, repeated suspended in cold ethanol, and dried.

21 g of the title compound are obtained.

HPLC analysis: 99.5% methylene-(6R)-tetrahydrofolic benzenesulfonate.

$[\alpha]^{25}_D = +120°$ (c=1% in DMF).

Example 7: 5,10-methylene-(6R)-THF toluene-4-sulfonate 27.75 g of pure (6S)-tetrahydrofolic acid toluene-4-sulfonate are dissolved in water by addition of sodium hydroxide solution. The solution is treated with 3.5 ml of 37% strength formaldehyde, and the reaction solution obtained is stirred into a concentrated aqueous solution of toluene-4-sulfonic acid.

23 g of the title compound having a purity (HPLC) of 98.6% are obtained.

In the examples, the glacial acetic acid functions merely as a solvent. Also, in Examples 1B, 3, 4, and 5, the ethanol merely served to lower the solubility of the products. In Example 2, ethanol was added to enhance and speed up the drying process. In Example 6, the ethanol functioned both as an optimizer for the drying process and to improve the purity of the product.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

We claim:

1. A methane-sulfonic acid, ethanesulfonic acid, phenylmethanesulfonic acid, camphor-10-sulfonic acid, naphthalene-1-sulfonic acid, naphthalene-2-sulfonic acid, naphthalene-1,5-disulfonic acid, or sulfuric acid addition salt of 5,10-methylene-(6R)-, (6R,S)- or (6S)-tetrahydrofolic acid.

2. A salt according to claim 1, selected from the group consisting of:

5,10-methylene-(6R)-tetrahydrofolic acid sulfate;
5,10-methylene-(6R,S)-tetrahydrofolic acid sulfate;
5,10-methylene-(6S)-tetrahydrofolic acid sulfate;
5,10-methylene-(6R)- (6R,S)-, (6S)-tetrahydrofolic acid benzenesulfonate;
5,10-methylene-(6R), (6R,S)-, and (6S)-tetrahydrofolic acid methanesulfonate.

3. A salt according to claim 2, wherein the salt is 5,10-methylene-(6R)-tetrahydrofolic acid sulfate.

4. A salt according to claim 2, wherein the salt is 5,10-methylene-(6R,S)-tetrahydrofolic acid sulfate.

5. A salt according to claim 2, wherein the salt is 5,10-methylene-(6S)-tetrahydrofolic acid sulfate.

6. A salt according to claim 2, wherein the salt is 5,10-methylene-(6R)-, (6R,S)-, or (6S)-tetrahydrofolic acid benzenesulfonate.

7. A salt according to claim 2, wherein the salt is 5,10-methylene-(6R), (6R,S)-, or (6S)-tetrahydrofolic acid toluene-4-sulfonate.

8. A salt according to claim 2, wherein the salt is 5,10-methylene-(6R)-, (6R,S)-, or (6S)-tetrahydrofolic acid methanesulfonate.

9. A pharmaceutical composition comprising a pharmaceutically acceptable salt of 5,10-methylene-(6R), (6R,S)-, or (6S)-tetrahydrofolic acid with sulfuric acid or a sulfonic acid and a pharmaceutically acceptable carrier, said sulfonic acid salt being a methane-sulfonic acid, ethane-sulfonic acid, phenylmethanesulfonic acid, caphor-10-sulfonic acid, naphthalene-1-sulfonic acid, naphthalene-2-sulfonic acid, naphthalene-1,5-disulfonic acid, or sulfonic acid addition salt of 5,10-methylene-(6R)-, (6R,S)-, or (6S)-tetrahydrofolic acid.

10. A pharmaceutical composition according to claim 9, wherein the salt is a methanesulfonic acid, ethane-sulfonic acid, phenylmethanesulfonic acid, camphor-10-sulfonic acid, naphthalene-1-sulfonic acid, naphthalene-2-sulfonic acid, or naphthalene-1,5-disulfonic acid addition salt of 5,10-methylene-(6R)-, (6R,S)-, or (6S)-tetrahydrofolic acid.

* * * * *

UNITED STATES PATENT AND TRADEMARK OFFICE
CERTIFICATE OF CORRECTION

PATENT NO. : 5,300,505
DATED : April 5, 1994
INVENTOR(S) : Hans R. MULLER et al.

It is certified that error appears in the above-indentified patent and that said Letters Patent is hereby corrected as shown below:

Claim 9; Column 8; Line 10:

Delete "caphor" and insert - - camphor - -

Signed and Sealed this

Second Day of August, 1994

BRUCE LEHMAN

*Attest:*

*Attesting Officer*     *Commissioner of Patents and Trademarks*